United States Patent
Buckberry

(10) Patent No.: US 9,592,029 B2
(45) Date of Patent: *Mar. 14, 2017

(54) VASCULAR ACCESS MONITORING DEVICE

(75) Inventor: Clive Buckberry, Warwick (GB)

(73) Assignee: Quanta Fluid Solutions Ltd., Warwickshire (GB)

( * ) Notice: Subject to any disclaimer, the term of this patent is extended or adjusted under 35 U.S.C. 154(b) by 316 days.

This patent is subject to a terminal disclaimer.

(21) Appl. No.: 13/393,429

(22) PCT Filed: Jun. 18, 2010

(86) PCT No.: PCT/GB2010/001202
§ 371 (c)(1),
(2), (4) Date: Jul. 12, 2012

(87) PCT Pub. No.: WO2010/146372
PCT Pub. Date: Dec. 23, 2010

(65) Prior Publication Data
US 2012/0271160 A1    Oct. 25, 2012

(30) Foreign Application Priority Data
Jun. 18, 2009   (GB) .................................. 0910467.0

(51) Int. Cl.
*A61B 5/05*   (2006.01)
*A61B 8/00*   (2006.01)
(Continued)

(52) U.S. Cl.
CPC .......... *A61B 8/4227* (2013.01); *A61B 8/0841* (2013.01); *A61M 1/3653* (2013.01);
(Continued)

(58) Field of Classification Search
USPC ........................................................ 600/424
See application file for complete search history.

(56) References Cited

U.S. PATENT DOCUMENTS 3,921,622 A  *  11/1975  Cole .............................. 600/437
3,972,320 A  *   8/1976  Kalman ........................ 600/519
(Continued)

FOREIGN PATENT DOCUMENTS

DE   196 09 698 A1   9/1997
DE   19802985        7/1999
(Continued)

OTHER PUBLICATIONS

May 18, 2015 Office Action in connection with U.S. Appl. No. 13/393,438.

*Primary Examiner* — Johanthan Cwern
*Assistant Examiner* — Amelie R Gillman
(74) *Attorney, Agent, or Firm* — Hahn Loeser & Parks LLP

(57) ABSTRACT

A monitoring device (1) is provided for monitoring the presence of a skin piercing vascular access device, for example a needle (4), the monitoring device comprising: a mount having an ultrasonic transmitter and an ultrasonic receiver therein; attachment means (3) for attaching the mount to a patient adjacent a vascular access point such that, in use, a vascular access device (4) entering the patient at the vascular access point, passes underneath a sensing section of the base; control electronics to monitor the signal received at the receiver, and wherein when the vascular access device is underneath said sensing section, ultrasound produced by said transmitter passes through the patient skin and is reflected by the patients body tissues and by the vascular access device (4), and when the vascular access device (4) is not underneath said sensing section, ultrasound produced by said transmitter passes through the patients skin and is reflected by the patients body tissue only, and wherein the control electronics detects the presence of a vascular access (4) device by performing a comparison on the received (Continued)

ultrasonic signal. The device (1) warns if a needle (4) becomes dislodged during a treatment.

30 Claims, 3 Drawing Sheets

(51) Int. Cl.
*A61B 8/08* (2006.01)
*A61M 1/36* (2006.01)
*A61B 5/00* (2006.01)
*A61B 5/02* (2006.01)
*A61M 5/168* (2006.01)

(52) U.S. Cl.
CPC ...... *A61M 1/3656* (2014.02); *A61M 5/16836* (2013.01); *A61B 5/0002* (2013.01); *A61B 5/02042* (2013.01); *A61B 8/0891* (2013.01); *A61B 8/4281* (2013.01); *A61B 8/4472* (2013.01); *A61M 5/16831* (2013.01); *A61M 2205/13* (2013.01); *A61M 2205/3375* (2013.01)

(56) References Cited

U.S. PATENT DOCUMENTS

| | | | |
|---|---|---|---|
| 4,205,686 A * | 6/1980 | Harris et al. | 600/459 |
| 4,534,756 A | 8/1985 | Nelson | |
| 4,648,869 A | 3/1987 | Bobo, Jr. | |
| 4,710,163 A | 12/1987 | Butterfield | |
| 4,771,792 A | 9/1988 | Seale | |
| 5,095,910 A | 3/1992 | Powers | |
| 5,727,550 A * | 3/1998 | Montecalvo | 600/386 |
| 5,882,300 A * | 3/1999 | Malinouskas et al. | 600/300 |
| 6,077,443 A | 6/2000 | Goldau | |
| 6,132,378 A * | 10/2000 | Marino | 600/459 |
| 6,216,029 B1 | 4/2001 | Paltieli | |
| 6,626,832 B1 * | 9/2003 | Paltieli et al. | 600/439 |
| 7,040,142 B2 | 5/2006 | Burbank | |
| 7,874,999 B2 | 1/2011 | Busby | |
| 8,114,043 B2 | 2/2012 | Muller | |
| 8,137,300 B2 | 3/2012 | Han et al. | |
| 8,187,184 B2 | 5/2012 | Muller et al. | |
| 8,192,388 B2 | 6/2012 | Hogard | |
| 8,197,431 B2 | 6/2012 | Bennison | |
| 8,221,320 B2 | 7/2012 | Bouton | |
| 8,348,850 B2 | 1/2013 | Frinak et al. | |
| 8,360,977 B2 | 1/2013 | Marttila et al. | |
| 8,529,490 B2 | 9/2013 | Wariar et al. | |
| 8,535,522 B2 | 9/2013 | Fulkerson et al. | |
| 8,597,505 B2 | 12/2013 | Fulkerson et al. | |
| 8,696,571 B2 | 4/2014 | Marttila et al. | |
| 8,708,908 B2 | 4/2014 | Bouton | |
| 8,708,946 B2 | 4/2014 | Han et al. | |
| 8,801,646 B2 | 8/2014 | Han et al. | |
| 8,926,544 B2 | 1/2015 | Hogard | |
| 8,974,394 B2 | 3/2015 | Frinak et al. | |
| 9,011,334 B2 | 4/2015 | Bouton | |
| 2003/0126910 A1 | 7/2003 | Burbank | |
| 2003/0128125 A1 | 7/2003 | Burbank et al. | |
| 2005/0010118 A1 | 1/2005 | Toyoda et al. | |
| 2005/0038325 A1 | 2/2005 | Moll | |
| 2007/0016053 A1 * | 1/2007 | Lo et al. | 600/459 |
| 2007/0073155 A1 | 3/2007 | Park et al. | |
| 2007/0167808 A1 | 7/2007 | Nozaki | |
| 2008/0108930 A1 | 5/2008 | Weitzel et al. | |
| 2008/0195021 A1 * | 8/2008 | Roger et al. | 604/4.01 |
| 2008/0195060 A1 | 8/2008 | Roger | |
| 2008/0221519 A1 * | 9/2008 | Schwach et al. | 604/116 |
| 2008/0275396 A1 | 11/2008 | Neerken et al. | |
| 2009/0082649 A1 * | 3/2009 | Muller et al. | 600/310 |
| 2009/0082676 A1 | 3/2009 | Bennison | |
| 2009/0088683 A1 | 4/2009 | Roger et al. | |
| 2010/0234786 A1 | 9/2010 | Fulkerson et al. | |

FOREIGN PATENT DOCUMENTS

| | | |
|---|---|---|
| DE | 198 48 235 C1 | 3/2000 |
| EP | 0 121 931 A2 | 10/1984 |
| EP | 0 232 599 A1 | 8/1987 |
| EP | 0 248 633 A2 | 12/1987 |
| EP | 0 328 163 A2 | 8/1989 |
| EP | 0 330 761 A1 | 9/1989 |
| EP | 0332 330 A2 | 9/1989 |
| EP | 0 361 793 A2 | 4/1990 |
| EP | 0 895 787 A1 | 2/1999 |
| EP | 1 472 973 A1 | 11/2004 |
| JP | 2005040518 A | 2/2005 |
| WO | WO 91/00113 | 1/1991 |
| WO | WO 97/10013 | 3/1997 |
| WO | WO 99/29356 | 6/1999 |
| WO | WO 2008/100671 A1 | 8/2008 |
| WO | WO 2009/024333 A1 | 2/2009 |
| WO | WO 2009/038834 A1 | 3/2009 |
| WO | WO 2010/089130 A1 | 8/2010 |

\* cited by examiner

VASCULAR ACCESS MONITORING DEVICE

CROSS-REFERENCE TO RELATED APPLICATIONS

This application claims priority from PCT/GB/2010/001202 filed on Jun. 18, 2010 and from GB 0910467.0 filed Jun. 18, 2009, which are hereby incorporated by reference in their entireties.

BACKGROUND OF THE INVENTION

1. Field of the Invention

This invention relates to vascular access monitoring, in particular it relates to a device and method for monitoring for the presence of a needle or cannular to determine if it becomes dislodged from a patient.

2. State of the Art

In a number of medical treatment regimes it is necessary to have access to the vascular system through a skin piercing, for example in drug infusion or blood processing treatments like dialysis.

It can be very important to know if a needle becomes dislodged from a patient, and in some cases a dislodged needle can cause serious medical consequences, for example dislodgement of a needle providing life supporting drugs, if not detected could even result in death, as could dislodgement of a blood return needle in a hemodialysis treatment whereby the dialyser can pull blood from the body but not return it. This is especially dangerous in overnight dialysis while the patent is asleep as they would not see the blood escaping.

Several devices have been proposed for detecting if a needle becomes dislodged from a patient, for example in hemodialysis sensors have been used which look at the effect of the presence of a needle on an electric circuit, for example as described in US2005/0038325. Another known device is described in DE 198 02 985 which discloses the use of an optical reflected signal to detect if the needle has become dislodged. The needle has a reflector mounted thereon to reflect an infra red signal from a transmitter back to a receiver. In this device the adaptation of the needle is required which is highly undesirable as it requires a change to a cheap part which is an accepted standard part across the industry.

SUMMARY OF THE INVENTION

It is the purpose of the present invention to provide an alternative to the known sensors that can be used with a standard needle or cannular.

According to a first aspect of the present invention there is provided a monitoring device for monitoring the presence of a skin piercing vascular access device, the monitoring device comprising:
  a mount having an ultrasonic transmitter and an ultrasonic receiver therein;
  attachment means for attaching the mount to a patient adjacent a vascular access point such that, in use, a vascular access device entering the patient at the vascular access point, passes underneath a sensing section of the base;
  a control circuit to monitor the signal received at the receiver, and wherein
  when the vascular access device is underneath said sensing section, ultrasound produced by said transmitter passes through the patient skin and is reflected by the patients body tissues and by the vascular access device, and
  when the vascular access device is not underneath said sensing section, ultrasound produced by said transmitter passes through the patients skin and is reflected by the patients body tissue only, and wherein
  the control electronics detects the presence of a vascular access device by performing a comparison on the received ultrasonic signal.

Preferably the device periodically emits an ultrasonic pulse and receives the reflected ultrasonic signal. When the vascular access device, e.g. a needle, is located beneath the sensing section it will reflect a different amount of the ultrasonic pulse than the tissue alone would. In this manner, by comparing subsequent received signals, a change in the received signal can be identified and a warning can be raised that the vascular access device has become dislodged.

Preferably the control electronics monitor the received signal received within in a particular time window, that time window being based on a maximum and minimum expected time of flight of the ultrasonic pulse from the transmitter, to the needle and back to the receiver. Preferably the window exceeds the expected window by a factor relating to a margin of error.

Preferably the sensor is configured to identify ultrasonic reflections from first and second surfaces, one of which is the needle, and the sensor detects a change in the received signals. Preferably the second surface is a deeper part of the body, e.g. a bone.

In one preferred arrangement the amplitude of the reflected signal changes dependant on the presence of the vascular access device.

Preferably an ultrasonic gel is used between the device and the patients skin to effectively ultrasonically couple the device to the patient. In one arrangement this coupling gel may be applied directly to the skin.

In a preferred arrangement the device further comprises a thin flexible gel pack, comprising an ultrasonic coupling gel, encapsulated within a flexible membrane, for insertion between the device and the skin. Preferably the gel pack has a thin flexible outer membrane that conforms easily to the skin thereby, in use, conforming to the contours of the patient's skin.

In this arrangement the flexible outer membrane prevents the ultrasonic coupling gel, which is usually water based, from evaporating over time. While normal gels applied to the skin are very useful for short term use, in some applications such as nocturnal dialysis, it may be necessary to monitor for dislodgement of the needle over a prolonged period of time, the water base of the ultrasonic gel will evaporate and eventually ultrasonic coupling may be lost resulting in false alarms. By encapsulating the ultrasonic gel in a thin pack the evaporation can be prevented or minimised, thereby overcoming the problem of gel evaporation.

In a preferred arrangement the attachment means comprises a strap to pass around a section of the patients body, for example an arm.

In one preferred arrangement the device is provided with an electrical connection for connecting the device to a medical apparatus, for example a dialysis machine.

In an alternative preferred arrangement the device has a wireless transceiver for connection to a medical apparatus. In this manner, if dislodgement of the vascular access device is sensed then this can be transmitted to the medical apparatus which can take appropriate action, i.e. it may sound a warning or stop an automated medical process.

Preferably the device has control electronics configured to periodically receive an interrogation from a medical apparatus to do a self diagnosis check, to carry out a self diagnosis check and to send a signal to the medical apparatus indicative that the diagnosis check was successful and the device is working properly.

In a preferred arrangement the ultrasonic transmitter is a piezo transmitter.

Preferably the transmitter and receiver comprise a single transceiver.

Preferably the device further comprises a power source. Preferably the power source is a re-chargeable battery and more preferably the re-chargeable battery is wirelessly re-chargeable and is fully encapsulated within the device. In this manner the device can easily be sanitised between uses.

According to a second aspect of the invention there is provided a thin flexible gel pack for use with the device of the first aspect of the invention, comprising:
an ultrasonic coupling gel, encapsulated within a flexible membrane and wherein the flexible membrane allows the passage of ultrasound therethrough.

Preferably the gel pack comprises two planar sides of flexible membrane material joined around their edges to encapsulate the gel therein.

In use the thin flexible gel is inserted between the device and the skin to ultrasonically couple the device to the patient's skin. The flexible membrane prevents the ultrasonic coupling gel, which is usually water based, from evaporating over time. While normal gels applied to the skin are very useful for short term use, in some applications such as nocturnal dialysis, it may be necessary to monitor for dislodgement of the needle over a prolonged period of time, the water base of the ultrasonic gel will evaporate and eventually ultrasonic coupling may be lost resulting in false alarms. By encapsulating the ultrasonic gel in a thin pack the evaporation can be prevented or minimised, thereby overcoming the problem of gel evaporation.

Preferably the gel pack has a thin flexible outer membrane that conforms easily to the skin thereby, in use, conforming to the contours of the patient's skin.

Preferably the gel pack has characteristics specific to the device for which it is intended to be used with. Preferably the flexible membrane has a thickness equal to, or less than one third of the wavelength of the ultrasound transmitted from the device. Preferably the composition of the gel is such that it has an optimum transmission frequency substantially that of the transmission frequency of the device with which it is intended to be used. More preferably it is composed to have an optimum transmission frequency in the range of 100 kHz to 2 MHz.

In one preferred embodiment the flexible membrane prevents evaporation of water therethrough.

In another preferred embodiment the flexible membrane is semi permeable, and permits the slow evaporation of water therethrough. More preferably the gel pack is provided in a sealed outer package, the outer package preventing evaporation from the gel. More preferably the membrane retards evaporation such after removal from the outer package the gel pack retains sufficient gel therein to function for at least 12 hours before its ultrasonic coupling properties become diminished.

In this manner the ultrasonic coupling properties of the gel pack can be allowed to diminish over time. Therefore, if the outer packaging becomes compromised, for example in transit, and the gel will slowly evaporate such that by the time it is used it should not function. Also, as the packs are a consumable part, near a skin puncture site, it is advantageous to provide a necessity for it to be changed on a time basis, and also that the pads can not be re-used from one patient to another. The time based degradation discourages such re-use.

The invention will now be described, by way of example, with reference to the following drawings.

BRIEF DESCRIPTION OF THE DRAWINGS

FIG. 3 is shows a typical ultrasonic pulse emitted by the device.

FIG. 4A shows a typical reflection of the ultrasonic pulse by the patient's body when a metal needle is not present, and FIG. 4B shows a typical reflection of the ultrasonic pulse when a metal needle is present.

DETAILED DESCRIPTION OF THE PREFERRED EMBODIMENTS

Figure 1:
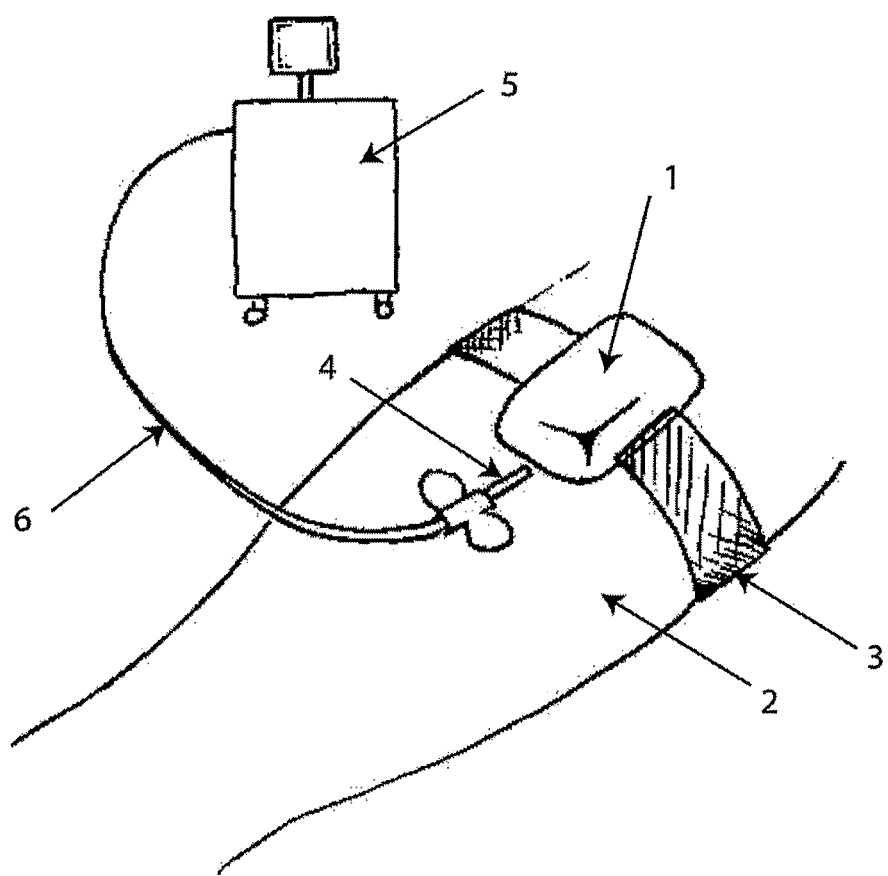
FIG. 1 is a perspective view of one embodiment of the device in use

Referring to FIG. 1 the device 1 is shown attached to a patient's arm 2 by means of an attachment strap 3. The device 1 is located adjacent the entry point of a needle 4 which is connected to a medical apparatus 5 by means of a conduit 6. The medical apparatus 5 can be used to either add fluid to or remove fluid from the patient via the needle 4.

Figure 2:
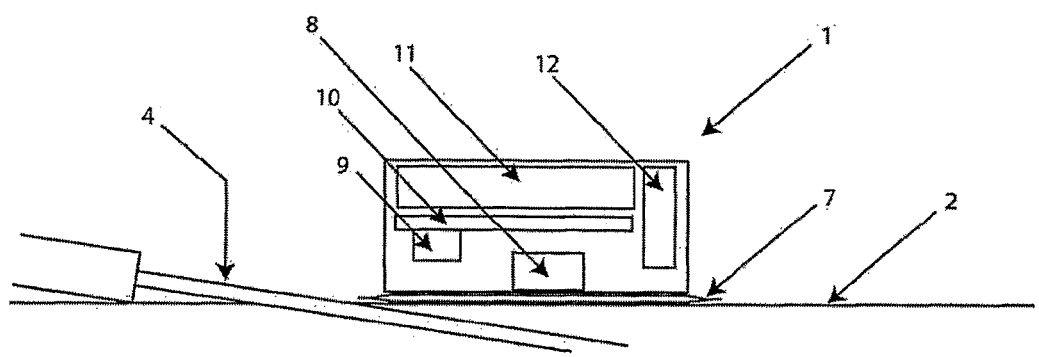
FIG. 2 is a cross section through same embodiment of the device in use.

Referring to FIG. 2 a cross section through the device in use is shown. The device 1 is positioned adjacent a patients arm 2 and between the patent's arm 2 and the device 1 is a thin gel pack 7 which comprises an ultrasonic coupling gel in a thin flexible plastic pouch. The gel pack 7 conforms to the surface of the patient's arm 2 and to the device 1 such that the space between the patients arm 2 and the device 1 is substantially filled with ultrasonic coupling gel. In use an ultrasonic transceiver 8 transmits an ultrasonic pulse through the gel pack and into the patient's arm 2. The gel pack 7 has walls made of a flexible membrane that has a thickness less than one third of the wavelength of the ultrasound transmitted from the device and the composition of the gel is such that it has an optimum transmission frequency substantially that of the transmission frequency of the device. The patient's arm will absorb some of the ultrasonic signal and reflect some of the signal. The transceiver also receives the reflected signal. The transceiver is connected to control electronics 10 which control the transmitter to transmit ultrasound and receive signals indicative of the received reflected signal from the transceiver 8. The control electronics then compare the received signal, either to the transmitted signal or to a model signal stores in storage means 9 connected to the control electronics 10 to detect if it shows characteristics relating to absorption and reflection by the patient's arm 2, or if it also shows characteristics relating to reflection by a needle 4. Signals relating to a needle 4 will be clearly distinguishable from signals relating to just the patients body as a needle 4, in particular a metal needle as is commonly used, will reflect a much greater amount of ultrasound. The control device is powered by a battery 11 which is encapsulated within the device 1. The battery may be recharged by an inductive recharger. In this way the battery can be recharged without needing to open the device to remove the battery. Furthermore, as the device is totally encapsulated it is easy to clean and/or sanitise between uses.

The device 1 further comprises a wireless communications module 12 by which the device can wirelessly communicate with the control system of a medical apparatus. In this way, if the needle becomes dislodged from the patient, the device 1 senses it and sends a signal t the medical apparatus to which the needle 4 is connected. He apparatus can then take appropriate action, for example it may sound a warning and/or may stop the medical process using the needle. For example, if the needle is being used to infuse drugs into a patient then if the needle 4 becomes dislodged then the medical apparatus can sound a warning to alert a nurse and can also stop the dispense of drugs through the needle 4.

Figure 3:
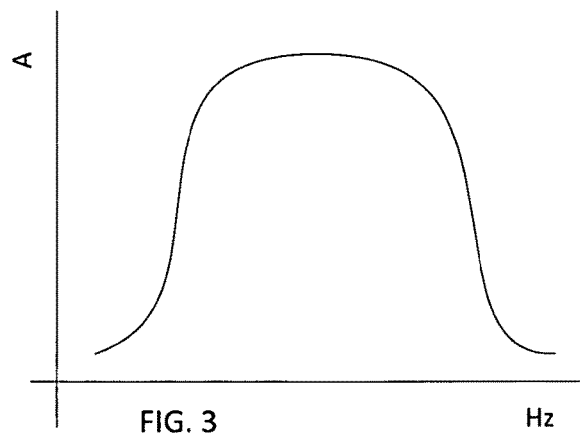
FIGS. 3, 4A and 4B are diagrams of ultrasonic signals.
Figure 4A:
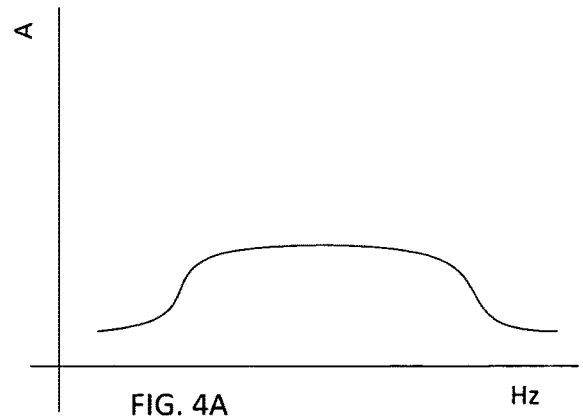
Figure 4B:
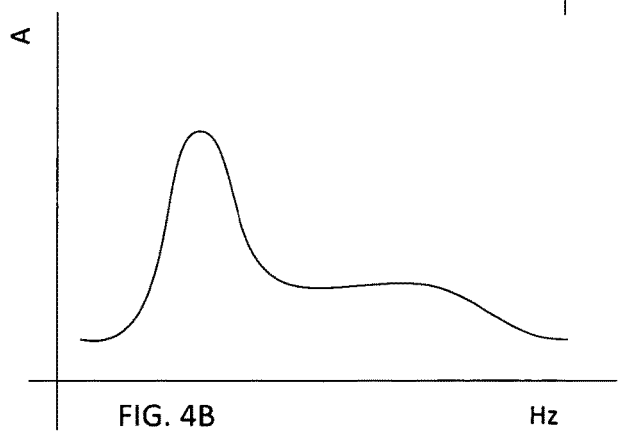

Referring to FIGS. 3, 4A and 4B, signal comparisons typical of those used in the device are shown. FIG. 3 shows a typical ultrasonic pulse emitted by the device. FIGS. 4A and 4B show two signals, one in FIG. 4A relating to the reflection of ultrasound by the patient's body when a metal needle is not present and the other in FIG. 4B showing how this changes when a metal needle is present. The control electronics can compare the shape of the received signals and easily identify whether there is a needle present or not.

Other embodiments will be obvious to the person skilled in the art and are included in this invention, for example, the wireless connection could be replaced with a wires connection and the battery could be replaced with a connection to a remote power source.

The invention claimed is:

1. A monitoring device for continuously monitoring the presence of an unattended skin piercing vascular access device, the monitoring device comprising:
   an ultrasonic transmitter configured to transmit an ultrasound signal pulse;
   a sensing section having an ultrasonic receiver configured to receive a reflected ultrasound signal;
   attachment means for attaching the monitoring device to a patient adjacent a vascular access point such that, in use, a vascular access device entering the patient at the vascular access point passes underneath the sensing section of the monitoring device; and
   control electronics configured so that, in use, the control electronics activate the transmitter to transmit the ultrasound signal pulses, and monitor an amplitude of the reflected ultrasound signal received by the receiver to determine whether the received reflected ultrasound signal was reflected only by the patient's body tissue or, alternatively, was reflected by both the patient's body tissue and the vascular access device that has been inserted underneath the sensing section;
   wherein, when the vascular access device is underneath said sensing section, the ultrasound signal pulses transmitted by said transmitter pass through the patient's skin and are reflected by the patient's body tissues and by the vascular access device, and when the vascular access device is not underneath said sensing section, the ultrasound signal pulses transmitted by said transmitter pass through the patient's skin and are reflected by the patient's body tissue only;
   wherein the determination by the control electronics of whether the ultrasound signals received by the receiver were reflected only by the patient's body tissue consists essentially of comparing the amplitude of the reflected ultrasound signals across a frequency spectrum received by the receiver to a control signal, and detecting whether there is a difference in amplitude between the reflected ultrasound signals received by the receiver and the control signal; and
   wherein, if the difference is detected, the control electronics automatically take appropriate action as a consequence of dislodgement of the vascular access device; and
   wherein the appropriate action comprises at least one of generating a warning signal that the vascular access device has become dislodged and stopping a medical procedure using the vascular access device.

2. The device according to claim 1, wherein the control electronics are configured so that, in use, the ultrasonic signal pulses transmitted by the ultrasonic transmitter are transmitted periodically.

3. The device according to claim 1, wherein:
   the control electronics monitor the reflected ultrasound signals received by the receiver within a particular time window, that time window being based on a maximum and minimum expected time of flight of the ultrasound signal pulses from the transmitter, to the vascular access device and back to the receiver.

4. The device according to claim 3, wherein: the particular time window exceeds an expected window, between the minimum expected time of flight and the maximum expected time of flight, by a factor relating to a margin of error.

5. The device according to claim 1, wherein the control signal is an ultrasound signal previously received by the receiver.

6. The device according to claim 1, wherein the control signal is an ultrasound signal transmitted by the transmitter.

7. The device according to claim 1, wherein the control signal is a model signal.

8. The device according to claim 1, further comprising:
   an ultrasonic coupling means for, in use, ultrasonically coupling the device to the patient's skin.

9. The device according to claim 8, wherein:
   the ultrasonic coupling means comprises a coupling gel encapsulated in a flexible pack.

10. The device according to claim 9, wherein:
    the flexible pack has a thin outer membrane such that, in use, the outer membrane conforms substantially to contours of the patient's skin, thereby substantially filling any space between the monitoring device and the patient's skin.

11. The device according to claim 1, wherein the attachment means comprises a strap to pass around a section of the patient's body.

12. The device according to claim 1, further comprising:
    an electrical connection for connecting the monitoring device to a medical apparatus.

13. The device according to claim 1, further comprising:
    a wireless transceiver for wireless communication with a medical apparatus.

14. The device according to claim 1, wherein the appropriate action comprises the generating of the warning signal indicating that the vascular access device has become dislodged.

15. The device according to claim 1, wherein:
    the control electronics are configured to periodically receive an interrogation to perform a self diagnosis check, to carry out the self diagnosis check, and to signal the device is working properly.

16. The device according to claim 1 wherein:
    the ultrasonic transmitter is a piezo transmitter.

17. The device according to claim 1, wherein:
    the transmitter and receiver comprise a single transceiver.

18. The device according to claim 1, further comprising: a power source.

19. The device according to claim 18, wherein: the power source is a re-chargeable battery.

20. The device according to claim 19, wherein: the re-chargeable battery is wirelessly re-chargeable and is fully encapsulated within the monitoring device.

21. A kit comprising:
a monitoring device in accordance with claim 1 for continuously monitoring the presence of an unattended skin piercing vascular access device; and
an ultrasonic coupling gel, encapsulated within a flexible membrane to form a thin flexible gel pack; and
wherein the flexible membrane allows passage of ultrasound therethrough.

22. A kit according to claim 21, wherein: the flexible membrane comprises two planar sides of flexible membrane material joined around their edges.

23. A kit according to claim 21, wherein a side of the flexible membrane intended to be placed adjacent the patient's skin comprises thin flexible membrane material that, in use, conforms substantially to contours of the patient's skin.

24. A kit according to claim 21, wherein: the flexible membrane has a thickness equal to, or less than one third of, a wavelength of the ultrasound signal pulse transmitted from the ultrasonic transmitter.

25. A kit according to claim 21, wherein: the ultrasonic coupling gel is characterised in that it has a transmission frequency optimised to be substantially that of a transmission frequency of the ultrasound signal pulse transmitted by the ultrasonic transmitter.

26. A kit according to claim 25, wherein: the ultrasonic coupling gel has an optimum transmission frequency in a range of 100 kHz to 2 MHz.

27. A kit according to claim 21, wherein: the flexible membrane prevents evaporation of water therethrough.

28. A kit according to claim 21, wherein: the flexible membrane is semi permeable, and permits slow evaporation of water therethrough.

29. A kit according to claim 28, further comprising: a sealed outer package in which the gel pack is provided, the outer package preventing evaporation from the ultrasonic coupling gel.

30. A kit according to claim 29, wherein: the flexible membrane retards evaporation such that, after removal from the outer package, the gel pack retains sufficient ultrasonic coupling gel therein to function fully for at least 12 hours before its ultrasonic coupling properties become diminished to an extent that coupling performance is affected.

* * * * *